SUGAR CANE
Filed June 28, 1962 3 Sheets-Sheet 1
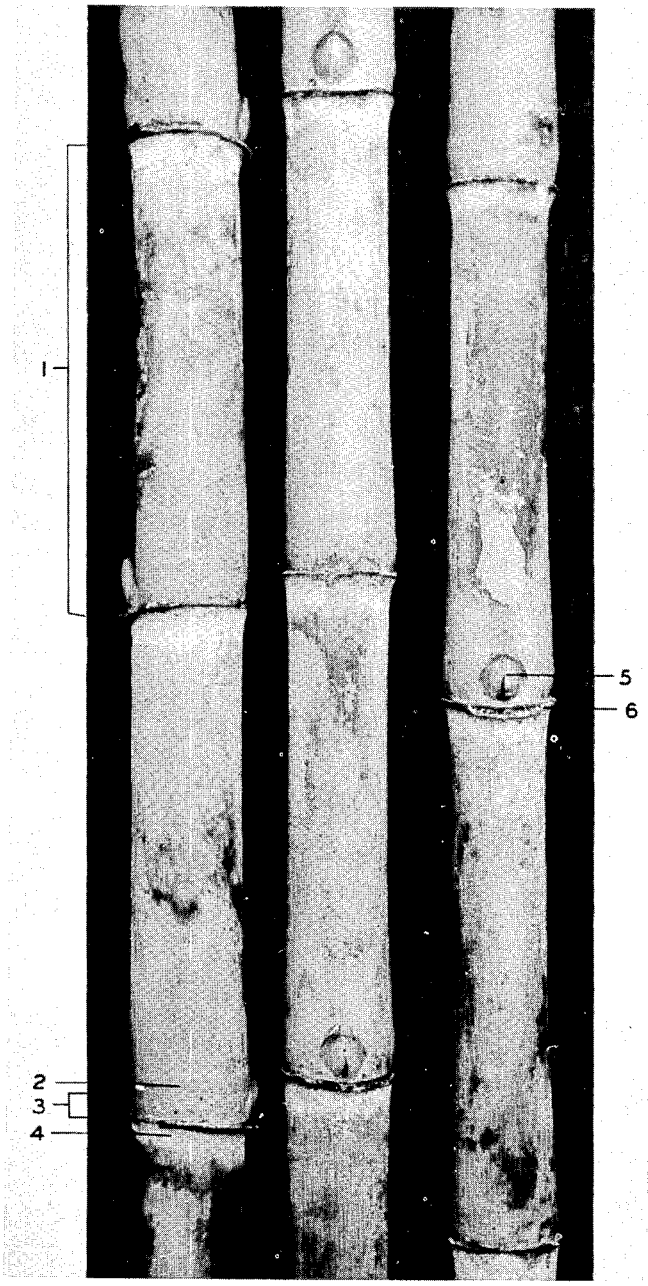
FIG. I
INVENTORS
LESLIE M. WEETMAN
BENJAMIN A. BOURNE
BY Cushman, Darby & Cushman
ATTORNEYS SUGAR CANE
Filed June 28, 1962 3 Sheets-Sheet 2
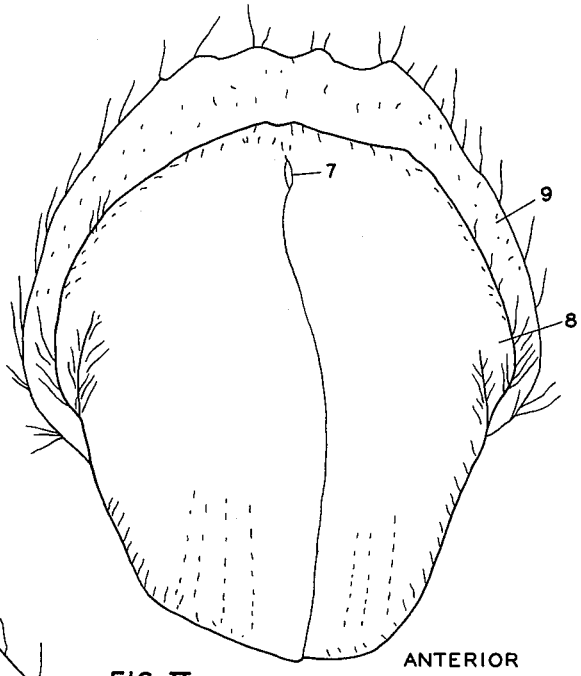
FIG. II
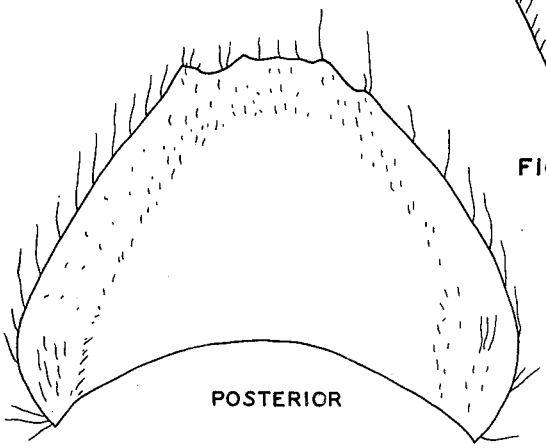
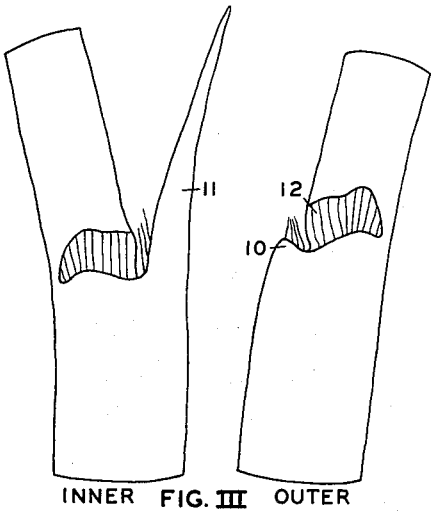
FIG. III
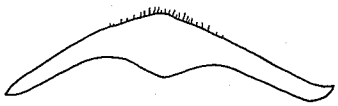
FIG. IV
INVENTORS
LESLIE M. WEETMAN
BENJAMIN A. BOURNE
BY Cushman, Darby & Cushman
ATTORNEYS

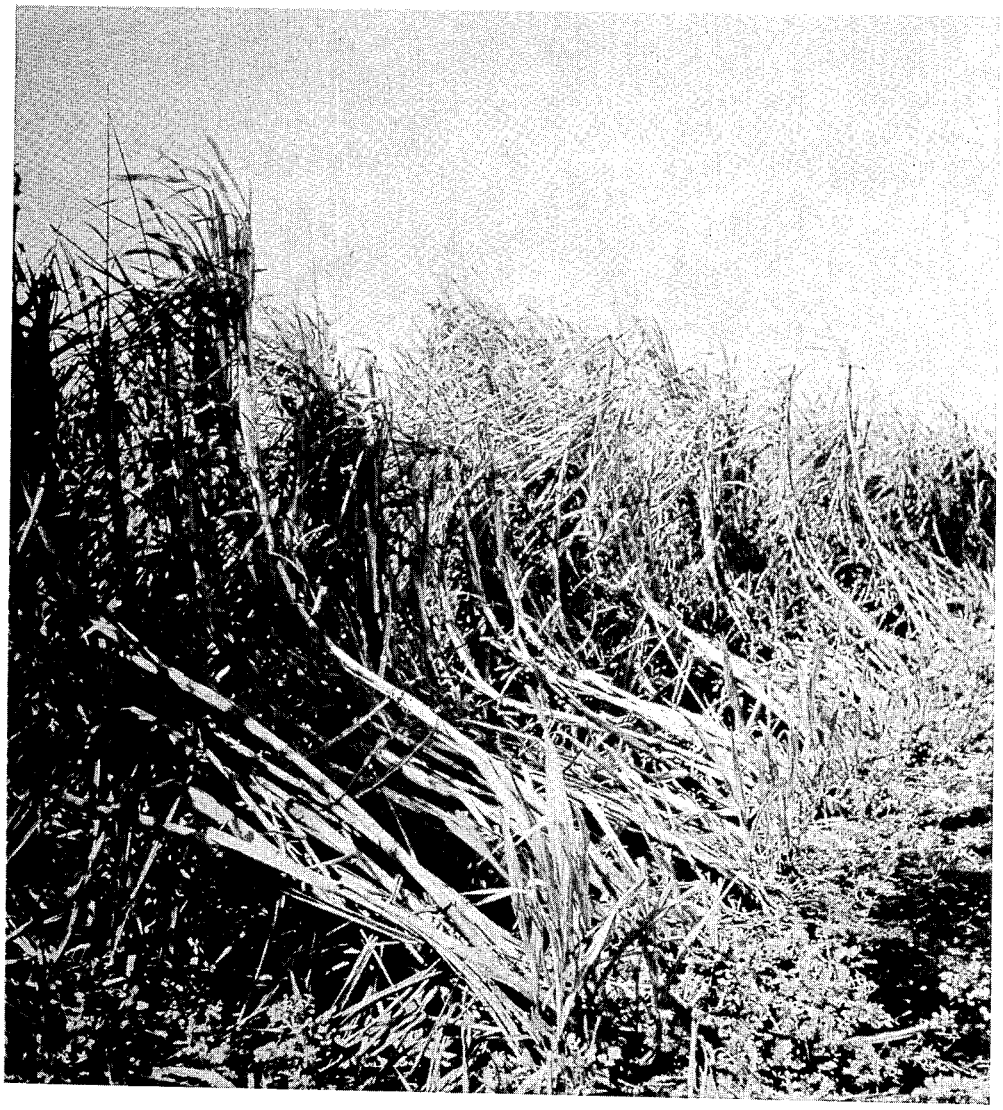
FIG. V
INVENTORS
LESLIE M. WEETMAN and
BENJAMIN A. BOURNE
BY Cushman, Darby & Cushman

United States Patent Office

Plant Pat. 2,461
Patented Dec. 1, 1964

2,461
SUGAR CANE

Leslie M. Weetman and Benjamin A. Bourne, Clewiston, Fla., assignors to United States Sugar Corporation, Clewiston, Fla., a corporation of Delaware

Filed June 28, 1962, Ser. No. 206,111
1 Claim. (Cl. Plt.—89)

This new variety of sugar cane originated as a seedling under a long established continuous program of crossing suitable parent canes and selecting desirable progeny. Both parent canes, consisting of the variety designated Cl. 41–142 (wherein "Cl." designates the growing place—Clewiston, Florida; 41 designates the year that the particular variety was first originated—1941; and 142 designates the distinctive number assigned to that variety; this form of designation is now well known in the art) as female and the variety designated Cl. 41–106 as male, were produced in 1941 and were then selected for crossing and the development of this new variety by combining their valuable characteristics during the fall of 1948 at Clewiston, Florida.

Subsequent propagation of this variety under an identifying number Cl. 49–198 by the inventors for the purpose of obtaining data on productivity, disease and pest resistance and other characteristics has been by asexual means, comprising stem cuttings. This propagation was carried out at Clewiston, Florida. This new variety is very early in maturity and very high in sucrose content throughout the normal Florida harvest period from late October until late April. In a replicated trial over a three-year period on low-mineral organic soil, the average sucrose content recoverable in percent by weight of the cane in late October and early November was approximately 23% above that of the standard variety of cane commonly referred to as Cl. 41–223, now being grown in south Florida, (see Table I). When harvested in January, the percent yield of 96° sugar was still 13% above that of the standard cane, (see Table I). Our new variety also has a higher sucrose content than C.P. 52–68 as shown by the data in Table II from a different trial. In ratoon-stunting-free plots, percent yields of 96° sugar for Cl. 49–198 were 43% above those for C.P. 52–68 for plant cane in November. By January, the difference had increased to 57%, and on the first stubble crop, the difference in favor of Cl. 49–198 was 41%. Comparative results on diseased plots indicated even greater superiority of Cl. 49–198. Thus, this new cane will be of great value for sugar production at the very beginning of the harvest season, and it can also be expected to mature well on so-called "cold" lands located several miles away from the protective climatic influence of large bodies of water in south Florida where the normal growing cycle is rather short due to early and late freezes during the winter and where organic soils of rather low mineral content, high in nitrogen, frequently exist and contribute to very slow maturity in the case of most cane varieties. Although this new variety may yield slightly fewer tons of cane per acre than the present standard variety, nevertheless, because of its very high sucrose content, it will produce more sugar per acre when harvested early and fully as much as the standard variety when harvested late, (see Table I). Thus the cutting, loading, hauling and milling costs will be substantially less for a given quantity of sugar produced.

TABLE I

*Comparative Yields of Cl. 41–223 and Cl. 49–198*

| Mean Yields of 96° Sugar, Percent Cane, on Following Dates— | Cl. 41–223 | Cl. 49–198 | Least Significant Difference |
|---|---|---|---|
| Early Analyses: | | | |
| Nov. 3, 1955 (Plant Cane) | 9.50 | 11.28 | .62 |
| Nov. 5, 1956 (1st Stubble) | 11.01 | 13.78 | .53 |
| Oct. 24, 1957 (2d Stubble) | 10.93 | 13.59 | .53 |
| 3-Year Means | 10.48 | 12.88 | .42 |
| Late Analyses: | | | |
| Jan. 10, 1956 (Plant Cane) | 12.14 | 13.94 | .81 |
| Jan. 11, 1957 (1st Stubble) | 12.41 | 14.15 | .57 |
| Jan. 30, 1958 (2d Stubble) | 12.80 | 14.25 | .39 |
| 3-Year Means | 12.45 | 14.11 | .44 |
| Tons Cane Per Acre: | | | |
| Harvest Dates— | | | |
| Feb. 6, 1956 (Plant Cane) | 33.70 | 30.90 | 4.30 |
| Jan. 14, 1957 (1st Stubble) | 47.51 | 38.39 | 3.77 |
| Feb. 20, 1958 (2d Stubble) | 39.86 | 38.31 | 4.40 |
| 3-Year Totals | 121.07 | 107.60 | 9.35 |
| Tons Sugar Per Acre: | | | |
| Estimate based on early analyses and tons cane at harvest— | | | |
| Plant Cane | 3.20 | 3.49 | ---------- |
| First Stubble | 5.23 | 5.29 | ---------- |
| Second Stubble | 4.36 | 5.21 | ---------- |
| 3-Year Totals | 12.79 | 13.99 | ---------- |
| Based on Late Analyses— | | | |
| Plant Cane | 4.09 | 4.30 | .54 |
| First Stubble | 5.90 | 5.43 | .50 |
| Second Stubble | 5.11 | 5.46 | .56 |
| 3-Year Totals | 15.10 | 15.19 | 1.15 |

The stalks of this variety are of medium-small diameter with a fiber content approximately 5.9 percent lower than that of Cl. 41–223, the standard cane now in commercial use in south Florida. This represents a distinct advantage to sugar mill operators, because the quantity of cane millable daily by mechanical crushing rolls is directly proportional to the fiber content of the sugar cane, therefore a mill can grind more tons of our new cane in a day. In milling operations, each ton of bone-dry fiber leaving the milling train normally carries with it substantial quanties of sucrose (approximately 8 percent by weight). With a mill grinding 7000 tons cane daily of the standard cane having 10.1 percent fiber (dry), 707 tons of bone-dry fiber is produced daily. A loss of 8 percent sucrose in the bone-dry fiber would mean a daily loss of 56.56 tons of sucrose worth, at 6¢ pound, $6,787.20. Since our new variety shows a fiber content of only 9.5 percent, it can be shown that by milling 7000 tons of this cane, a saving of $403.20 daily will be experienced, representing the lower loss of sucrose in the bone-dry fiber.

Germination of the buds on stem cuttings is satisfactory and ratooning is good, even when the variety is infected with the ratoon stunting virus.

Table II summarizes yield data obtained in a randomized block trial with treatments replicated five times, using 1/50 acre plots, planted December 17, 1959, and carried to completion for two crop cycles, using Cl. 49–198 and C.P. 52–68 in the same experiment. Seed-pieces of each variety on the one hand were infected with and on the other hand freed from the ratoon stunting (RSD) virus by means of hot air treatment at 50° C. for 24 hours. C.P. 52–68 was released by the United States Department of Agriculture for commercial culture in Louisiana in 1958 and for cultivation in Florida in 1962. (See News Release of U.S.D.A. CR–26–62.) In the very early analysis for percent yield of 96° sugar on November 21, 1960, a slight significant reduction in this factor was noted following the heat treatment of Cl. 49–198 for the elimination of RSD virus. However, no significant differences either in percent yield of 96° sugar, tons of cane, or tons of recoverable sugar per acre occurred between diseased and healthy cane of this variety over a two crop cycle at the time of winter harvesting. The reference variety—C.P. 52–68 also showed no significant differences in any of the yield factors studied at the same time in regard to healthy and diseased cane.

Whether heat treated or not for RSD virus, the data in Table II show clearly that Cl. 49–198 significantly outyielded C.P. 52–68 in sugar per acre, both as plant cane and first stubble, on low mineral organic soil in the Florida Everglades. Combining the data from both crops, diseased cane of Cl. 49–198 gave significantly (2.27 tons) more sugar per acre, and healthy cane 2.48 tons more sugar per acre than C.P. 52–68.

TABLE II

*Comparative Experimental Research on Effect of Ratoon Stunting Disease on Yields of Cl. 49–198 and C.P. 52–68 (Planted 12/17/59 and Ratooned 1/24/61)*

DISEASE FREE PLOTS

| Factor [1] | Cl. 49–198 | | C.P. 52–68 | |
|---|---|---|---|---|
| | Plant Cane | 1st Stubble | Plant Cane | 1st Stubble |
| Percent Yield 96° Sugar | 10.66 (1) | ---------- | 7.44 (1) | ---------- |
| Percent Yield 96° Sugar | 12.81 (2) | 13.61 (3) | 8.14 (2) | 9.62 (3) |
| Tons Cane/Acre | 48.28 (4) | 37.35 (5) | 49.32 (4) | 39.82 (5) |
| Tons 96° Sugar/Ac | 6.18 (4) | 5.08 (5) | 4.01 (4) | 3.83 (5) |

DISEASED PLOTS

| | | | | |
|---|---|---|---|---|
| Percent Yield 96° Sugar | 11.57 (1) | ---------- | 7.71 (1) | ---------- |
| Percent Yield 96° Sugar | 13.30 (2) | 14.08 (3) | 8.06 (2) | 9.74 (3) |
| Tons Cane/Ac | 48.39 (4) | 34.87 (5) | 50.37 (4) | 41.81 (5) |
| Tons 96° Sugar/Ac | 6.43 (4) | 4.91 (5) | 4.06 (4) | 4.07 (5) |

[1] Analyses or weight records made on the following dates: (1) 11/21/60 (2) 1/10/61; (3) 1/16/62; (4) 1/24/61; (5) 1/24/62.

*Statistical data.*—Experimental records taken from a randomized block trial, treatments replicated 5 times. Plots 1/50 acre each, low mineral organic Everglades peat soil.

LEAST SIGNIFICANT DIFFERENCE AT 5% LEVEL

| Factor | Plant Cane | | 1st Stubble | |
|---|---|---|---|---|
| | Date | L.S.D. | Date | L.S.D. |
| Percent Yield 96° Sugar | 11/21/60 | 0.81 | ---------- | ---------- |
| Percent Yield 96° Sugar | 1/10/61 | 0.53 | 1/16/62 | 0.51 |
| Tons Cane/Ac | 1/24/61 | 2.71 | 1/24/62 | 4.53 |
| Tons 96° Sugar/Ac | 1/24/61 | 0.37 | 1/24/62 | 0.57 |

Heat treatment for ratoon stunting disease control is not recommended for this variety, because this has caused an average reduction in percent yield of 96° sugar over two crop cycles of approximately 0.48 point and in spite of average yields of cane per acre being 1.19 tons higher higher due to treatment, an average loss of 0.04 ton 96° sugar per acre resulted.

Observations on the effect of the heat treatment for ratoon stunting disease control on the flowering characteristics of this cane on organic soils have shown that there is no change initiated which causes the variety to flower either earlier or later than without this treatment.

In repeated tests for establishing the resistance of the new variety to the four strains of mosaic disease virus, namely "A," "B," "D" and "E," recorded in Florida, a minimum of 20 young plants three weeks old, grown from single-eye cuttings were used for inoculation each time, using a mixture of the extracted virus strains in equal parts and the most up-to-date means of artificial inoculation. At the same time each test was made, two similar batches of ten disease-free plants, each of an ordinary mosaic disease susceptible sugar cane variety, were observed as controls, one batch being inoculated with the same source of mixed inoculum and the other batch kept as non-inoculated controls. All comparative test work was done under screened greenhouse conditions, using identical steam sterilized soil and flats for growing all the test plants and insuring identical conditions of temperature, humidity, sunlight, soil fertility and irrigation in all cases. The number of positively infected plants in any one test series of the new variety of sugar cane never exceeded 7 precent after 50 days, whereas 100 percent of the inoculated controls became infected and exhibited severe leaf damage symptoms after 15 days. That the virus inoculum was potent and the control stock was disease-free was demonstrated by the rapid infection of all inoculated controls and the fact that none of the non-inoculated controls became infected.

From a milling standpoint, the expressed stalk juice of this new variety shows an exceptionally high content of phosphorus, being almost twich as high as that normally present in the standard cane variety and therefore it lends itself to good clarification without having to use supplemental quantities of this element. The calcium content of the juice of the new variety is high also, but is no higher than in the case of our standard variety, Cl. 41–223, so that the evaporator scaling problem will be no greater than in the case with Cl. 41–223.

In the drawings

FIGURE I is a photograph of approximate midsections of typical stalks, showing internode 1, growth ring 2, root band 3, wax ring 4, stem bud 5 and leaf scar 6.

FIGURE II shows anterior and posterior views of the stem bud, showing germ pore 7, inner wing 8 and outer wing 9.

FIGURE III is a view of the two separated and flattened halves of the upper part of a leaf sheath, showing the outer auricle 10, inner auricle 11 and the dewlap or blade joint 12.

FIGURE IV is a view showing the outline of a ligule after its removal from the inner surface of the leaf sheath.

FIGURE V is a photograph showing the semi-recumbent habit of growth of mature cane of our new variety.

Detailed Description

In the following detailed description of the new variety of sugar cane the terminology used in morphological description and numbering of hair groups is that employed by Artschwager. (See Sugarcane (*Saccharum officinarum* L.): Origin, Classification, Characteristics, and Descriptions of Representative Clones by Ernst Artschwager and E. W. Brandes. Agriculture Handbook No. 122. United States Department of Agriculture, 1958.) Color descriptions are made by referring to the plates of Maerz and Paul. (See A Dictionary of Color, second edition, by A. Maerz and M. Rea Paul. McGraw-Hill Book Company, 1950.)

*The Stalk (or Culm)*

*Habit of growth.*—The stalks are at first erect, but become semi-recumbert, (see FIGURE V), in fall and winter. The internodes are aligned so that the stalks are straight and not zigzag.

*Size.*—The stalks are usually 7 to 9 feet long, averaging 90.6 inches. They are elliptical in cross-section, averaging 22.4 x 24.3 millimeters in the middle. The larger diameter may vary from 21 to 27 millimeters.

*Flesh.*—Solid. The fiber content is low, averaging 9.5%. The color is approximately Maerz and Paul's designation 12–J–2 (absinthe yellow), but varies to 12–L–5 or 13–L–4, lighter near the center of the stalk.

*Internodes 1 (FIGURE I).*—Slightly conoidal in shape, but may be nearly cylindrical. The base often bulges slightly on the side opposite the bud. Internode length is 11 to 14 centimeters in the middle of the stalk, averaging 12.5 centimeters. Bud furrows are usually absent, but there is sometimes a slightly flattened area above the bud and shallow bud furrows may occur on lower internodes. Corky cracks or growth cracks are not evident except for occasional occurrence on lower internodes.

*Color.*—On portions of the stalk still protected by leaf sheaths, the basic color in the first inch or so above the growth ring is approximately Maerz and Paul's 10–F–2 (straw-color). Higher up on each internode, there is a heavy coating of wax which becomes progressively thicker and culminates in a prominent wax ring (FIGURE I–4) below the next node. This wax coating or bloom at first gives a grayish or whitish appearance, but this often becomes blackish over much of the internode due to mold growth. Portions of the stalk exposed to sunlight may turn green, then reddish to brownish, often approaching Maerz and Paul's 8–H–8 (Cordovan Brown).

*Growth ring 2 (FIGURE I).*—Tumescent. It is about 3 to 4 millimeters tall in the middle of the stalk. The color is just perceptibly darker than the color or the internode above. The color of the growth ring approaches Maerz and Paul's designation 11–F–3, but turns green when exposed to sunlight.

*Root band 3 (FIGURE I).*—The root band is somewhat obconoidal in shape. It is 8 or 9 millimeters tall on the bud side and 6 or 7 millimeters tall on the opposite side. The color is similar to the color of the base of the internode. The root band has two rows of root primordial.

*Leaf scar 6 (FIGURE I).*—The leaf scar protrudes and is depressed under the bud.

*Epidermal cells.*—Single pairs of short cells (consisting of one cork cell and one silica cell) alternate with long cells in a very regular pattern, which is clearly Artschwager's Type 1. There are occasional solitary cork cells, and occasionally two cork cells will be associated with a silica cell to form a group of three short cells. There are approximately 750 short cell groups per square millimeter. Long cells average 12.0 microns in width; their ends are usually rectangular. No stomata were seen.

*Stem Buds*

*General characteristics.*—The buds are inserted above the leaf scar 5 (FIGURE I). The tips extend to the growth ring or above. The stem buds are not protruding or overly prominent and have an average size of about 9 millimeters wide by 10 millimeters long. The base of the prophyll is angular as in pentagonal buds, but the tip is broadly rounded (FIGURE II). The germ pore is located near the tip of the prophyll 7 (FIGURE II). The color of the buds is at first similar to the basic color of the internode, but often turns red in sunlight.

*Wings of the prophyll.*—Many buds appear to have two wings. The inner wing 8 (FIGURE II) is fleshy and is apparently a lobe of the prophyll. It is usually delimited by a furrow or juncture, but is highly variable. Typical hair groups occur along this juncture. The outer wing 9 (FIGURE II) is membranaceous and is often attached under the edge of the prophyll or inner wing. It has a broad blunt tip. Both inner and outer wings may be irregularly lobed. The wings are inserted below the middle of the prophyll.

*Pubescence.*—Usually not very abundant; highly variable. Rather long hairs of groups 4 and 15 occur sparsely on the margin; tufts of group 26 occur at the base of the wings. On the anterior side, short hairs of groups 6 and 12 may be fairly abundant or almost absent. There are generally some hairs of groups 1, 2 and 16, and sometimes 13. On the posterior surface, groups 19, 20, 21 and 22 are generally present in some degree. Group 10 apparently does not occur. Most hairs are appressed; all may be heavily coated with wax.

*The Leaf*

*The blade.*—The blade is ascending in habit. It is 4.3 to 6.2 centimeters wide, averaging 5.27 and is 120 to 157 centimeters long, averaging 136. The ratio of the length of the blade to the width of the blade is 26. The color of the blade approaches Maerz and Paul's 23–H–6 on its upper surface and 24–J–3 on its lower surface.

*The sheath.*—The sheaths have an average length of 28 centimeters. Group 57 hairs occur over a broad area and appear to coalesce with group 60 hairs present on underlying sheath edge below the inner auricle. These hairs are medium dense, appressed and spinelike and persist on old sheaths. Group 56 hairs (on margin) are usually absent. The sheath base is slightly decurrent in young shoots. The old sheaths mostly adhere to the stalks, but they usually strip off fairly easily.

*Dewlaps 12 (FIGURE III).*—The dewlaps have a shape that is variable, usually being squarish to squarish-subcrescent and sometimes squarish-deltoid. The dewlaps are usually dark-colored, often approaching Maerz and Paul's 15–L–4 (olive green) to 15–H–6. The outer surface usually has a grayish cast due to the encrustation of wax. It is covered rather densely with short hairs of group 58. These are longer and more dense near outer margin and are usually covered with wax. Dense pubescence usually covers the entire inner surface of the dewlap and extends across the midrib. The hairs are short near the upper margin of the dewlap, longer below and longer still and more dense near the midrib. The band across the midrib is as wide as the dewlap. Long hairs of group 51 on the margin of the dewlap together with group 54 on the margin of the auricle form a conspicuous tuft. There is usually no wax on the inner surface of the dewlap.

*Auricles.*—The outer auricle 10 (FIGURE III) is ascending transitional to short deltoid in shape. A conspicuous hair group 54 is found on the upper margin. The inner auricle 11 (FIGURE III) is long lanceolate in shape, and is 3 to 7 centimeters in length, averaging about 4.5. It is subtended by a tuft of group 54 hairs. Auricles and the sheath margins below them are often scarious.

*Ligules (FIGURE IV).*—Shape broad crescent with broad lozenge, 6 to 7 millimeters tall, 30 to 35 millimeters long. The ventral surface is glabrous and the dorsal surface is covered with closely adnate hairs of group 66. Group 61 hairs occur on the margin mainly over the midrib. These hairs reach 0.5 millimeter in length. Groups 65*a* and 55*a* are not evident.

*Inflorescence.*—This variety blooms rather sparsely and late in Florida (i.e. in January). The inflorescence is of medium size and the flowers are male sterile.

Important characteristics which, in combination, help to distinguish this new variety of sugar cane from all other known varieties are:

(1) Very early maturity.

(2) Very high sucrose content throughout the harvest season.

(3) High yield of sugar per acre.

(4) Resistance to ratoon stunt and mosiac diseases.

(5) Semi-recumbent habit of growth at maturity.

(6) Stalks which average 22.4 x 24.3 millimeters in diameter.

(7) Internodes elliptical in cross-section.

(8) Low fiber content of stalks.

(9) Stalks coated with a heavy bloom.

(10) Stem buds which are angular at the base and rounded at the top.

(11) Many buds with double wings.

(12) Sparse pubescence on buds.

(13) Absence of bud furrows except for occasional occurrence on lower internodes.

(14) Narrow root bands with only two rows of root primorida.

(15) Pattern of the stem epidermal cells very similar to Artschwager's Type 1.

(16) Broad area of persistent spine-like hairs on leaf sheaths.

(17) Leaf sheaths adhering past maturity.

(18) Dewlaps usually squarish to squarish-subcrescent in shape.

(19) Inner surface of dewlaps with dense pubescence which extends across the midrib.

(20) Long lanceolate inner auricles.

(21) Shape of ligule: broad crescent with broad lozenge.

(22) Inflorescences occur rather sparingly and late in Florida.

(23) Flowers do not produce fertile pollen in Florida.

(24) Flowering habit on organic soil not changed by heat treatment of vegetative stalks at 50° C. for 24 hours for ratoon stunting disease control.

What is claimed is:

The variety of sugar cane herein shown and described, characterized particularly by its very early maturity, very high sucrose content, high yield of sugar per acre, resistance to ratoon stunting and mosaic diseases, medium-small diameter stalks, semi-recumbent habit of growth, distinctive shape of stem buds, distinctive pattern of stem epidermal cells, distinctive shape, and pubescence of dewlaps.

No references cited.

ABRAHAM G. STONE, *Primary Examiner.*